United States Patent
Will

(10) Patent No.: US 9,909,169 B2
(45) Date of Patent: Mar. 6, 2018

(54) ALLELE-SPECIFIC AMPLIFICATION OF NUCLEIC ACIDS USING BLOCKING OLIGONUCLEOTIDES FOR WILD TYPE SUPPRESSION

(71) Applicant: Roche Molecular Systems, Inc., Pleasanton, CA (US)

(72) Inventor: Stephen G. Will, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 437 days.

(21) Appl. No.: 14/574,181

(22) Filed: Dec. 17, 2014

(65) Prior Publication Data

US 2016/0177372 A1 Jun. 23, 2016

(51) Int. Cl.
*C12Q 1/68* (2006.01)

(52) U.S. Cl.
CPC ......... *C12Q 1/6858* (2013.01); *C12Q 1/6806* (2013.01)

(58) Field of Classification Search
CPC .................................................. C12Q 1/6858
USPC ........................................................ 435/6.1
See application file for complete search history.

(56) References Cited

U.S. PATENT DOCUMENTS

| | | | |
|---|---|---|---|
| 5,137,806 A | 8/1992 | Le Maistre et al. |
| 5,210,015 A | 5/1993 | Gelfand et al. |
| 5,521,301 A | 5/1996 | Wallace et al. |
| 5,595,890 A | 1/1997 | Newton et al. |
| 5,639,611 A | 6/1997 | Wallace et al. |
| 5,990,303 A | 11/1999 | Seela |
| 6,001,611 A | 12/1999 | Will |
| 7,135,291 B2 | 11/2006 | Sagawa et al. |
| 7,408,051 B2 | 8/2008 | Ma et al. |
| 8,071,338 B2 | 12/2011 | Newton |
| 2010/0099110 A1 | 4/2010 | Will et al. |

FOREIGN PATENT DOCUMENTS

| | | |
|---|---|---|
| EP | 0974672 | 4/2003 |
| EP | 2009007463 | 2/2010 |
| JP | 10279593 | 10/1998 |
| JP | 2966389 | 10/1999 |
| WO | 200043544 | 7/2000 |
| WO | 2007127992 | 11/2007 |
| WO | 2009019008 A1 | 2/2009 |

OTHER PUBLICATIONS

Ohta, Yuzo, et al., 2006, "Analysis of Chloroplast Genoms of Two Cytoplasmic Male Sterile Lines Derived from Interspecific Chimera and Intergeneric Somatic Hybrid in Brassicaceae", Breeding Sciences, 56:1-5.
Whitcombe, D. et al., Nature Biotech., vol. 17, pp. 804-807 (1999).
Newton, C.R. et al., Nucl. acids res., vol. 17, pp. 2503-2516 (1989).
Sapio, M. R. et al., Eur. J. Endocrinol., vol. 154, pp. 341-348 (2006).
Kwok, S. et al., PCR Meth. appl., vol. 3, pp. S39-S47 (1994).
Gaster, Jens, et al., 2005, "Tuning Single Nucleotide Discrimination in Polymerase Chain Reactions (PCRs): Synthesis of Primer Probes Bearing Polar 4'-C-Modifications and Their Application in Allele-Specific PCR", Chemistry: a European Journal, 11:1861-1870.

*Primary Examiner* — Jezia Riley
(74) *Attorney, Agent, or Firm* — David J. Chang

(57) ABSTRACT

A method is provided for allele-specific amplification, utilizing a blocking oligonucleotide including at least one nucleotide with a base covalently modified at the exocyclic amino group, the blocking oligonucleotide being perfectly complementary to a wild type (WT) sequence when hybridized forming a first complex having a first melting temperature (Tm), the blocking oligonucleotide being partially non-complementary, at one or more nucleotides, to a target mutant (MT) sequence when hybridized forming a second complex having a second melting temperature (Tm), wherein the first Tm is higher than the second Tm and having at least one nucleotide with a base covalently modified at the exocyclic amino group, wherein the blocking oligonucleotide becomes unhybridized from the target MT sequence during amplification but remains hybridized with the WT sequence inhibiting amplification of the WT sequence utilizing a polymerase lacking 5'-3' nuclease activity.

9 Claims, 1 Drawing Sheet

ALLELE-SPECIFIC AMPLIFICATION OF NUCLEIC ACIDS USING BLOCKING OLIGONUCLEOTIDES FOR WILD TYPE SUPPRESSION

FIELD OF THE INVENTION

The present invention relates to the field of nucleic acid amplification and specifically, to the field of allele-specific amplification.

BACKGROUND OF THE INVENTION

Allele-specific amplification of nucleic acids allows for simultaneous amplification and analysis of the target sequence. Allele-specific amplification is commonly used when the target nucleic acid has, or is suspected of having, one or more subpopulations with a variation (polymorphism) in its sequence. DNA polymorphisms are used in DNA profile analysis (forensics, paternity testing, tissue typing for organ transplants), genetic mapping, distinguishing between pathogenic strains of microorganisms, as well as detection of rare mutations, such as those occurring in cancer cells in the background of cells with normal DNA.

In a successful allele-specific amplification, the desired variant of the target nucleic acid is amplified, while the other variants are not, at least not to a detectable level. A typical allele-specific amplification assay involves a polymerase chain reaction (PCR) with at least one allele-specific primer designed such that primer extension occurs only when the primer forms a hybrid with the desired variant of the target sequence. When the primer hybridizes to an undesired variant of the target sequence, primer extension is inhibited.

Certain improvements for allele-specific amplification of nucleic acid targets have been proposed. Further improvements in the effectiveness and sensitivity of allele-specific amplifications for many clinically-relevant nucleic acid targets of nucleic acid targets are desirable, and the present disclosure provides related benefits.

SUMMARY OF THE INVENTION

In one embodiment, a method is provided for allele-specific amplification of a target sequence, which exists in the form of several variant sequences in a sample, including providing a blocking oligonucleotide comprising a 5' terminus, a 3' terminus, and at least one nucleotide with a base covalently modified at the exocyclic amino group, the blocking oligonucleotide being perfectly complementary to a wild type (WT) sequence when hybridized forming a first complex having a first melting temperature (Tm), the blocking oligonucleotide being partially non-complementary, at one or more nucleotides, to a target mutant (MT) sequence when hybridized forming a second complex having a second melting temperature (Tm), wherein the first Tm is higher than the second Tm, the blocking oligonucleotide being blocked at the 3' terminus prohibiting extension; and performing an amplifying step at a temperature higher than the second Tm but lower than the first Tm utilizing a polymerase lacking 5'-3' nuclease activity, the amplifying step comprising contacting the sample with a set of primers to produce an amplification product if the WT sequence and/or the target MT sequence is present in the sample, wherein the blocking oligonucleotide becomes unhybridized from the target MT sequence during the amplification step but remains hybridized with the WT sequence inhibiting amplification of the WT sequence. The nucleotide having a covalently modified base at the exocyclic amino group may be located at positions −5, −4, −3, −2 or −1 relative to the site of non-complementary nucleotide of the blocking oligonucleotide, or position 0 which would be at the site of non-complenenary.

In another embodiment, a kit is provided for allele-specific amplification of a target sequence, which exists in the form of several variant sequences, including a set of primers; and a blocking oligonucleotide comprising a 5' terminus, a 3' terminus, and at least one nucleotide with a base covalently modified at the exocyclic amino group, the blocking oligonucleotide being perfectly complementary to a wild type (WT) sequence when hybridized forming a first complex having a first melting temperature (Tm), the blocking oligonucleotide being partially non-complementary, at one or more nucleotides, to a target mutant (MT) sequence when hybridized forming a second complex having a second melting temperature (Tm), wherein the first Tm is higher than the second Tm.

In another embodiment, an oligonucleotide is provided for performing an allele-specific amplification of a target sequence, which exists in the form of several variant sequences, including a sequence a 5' terminus and a 3' terminus being blocked at the 3' terminus prohibiting extension, the sequence being perfectly complementary to a wild type (WT) sequence when hybridized forming a first complex having a first melting temperature (Tm), and being partially non-complementary, at one or more nucleotides, to a target mutant (MT) sequence when hybridized forming a second complex having a second melting temperature (Tm), wherein the first Tm is higher than the second Tm; and at least one nucleotide with a base covalently modified at the exocyclic amino group.

DETAILED DESCRIPTION OF THE INVENTION

Definitions

Figure 1A:
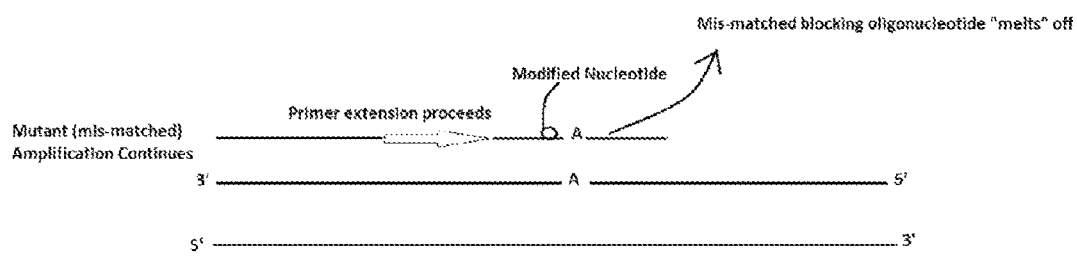
FIGS. 1A and 1B show a schematic diagram of an embodiment of an allele-specific amplification assay.

Unless defined otherwise, all technical and scientific terms used herein have the same meaning as commonly understood by one of ordinary skill in the art to which this invention pertains. In describing and claiming the present subject matter, the following definitions will be used.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49(10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphosphoroamidite linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895). Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034, 506. Nucleic acids containing one or more carbocyclic sugars are also included within the definition of nucleic acids (see Jenkins et al. (1995) Chem. Soc. Rev. pp. 169-176), and analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Helv. Chim. Ada 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (comprising at least one homocyclic ring, at least one heterocyclic ring, at least one aryl group, and/or the like) covalently linked to a sugar moiety (a ribose sugar or a deoxyribose sugar), a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to a 5' position of a sugar moiety of the nucleoside.

A "purine nucleotide" refers to a nucleotide that comprises a purine base, whereas a "pyrimidine nucleotide" refers to a nucleotide that comprises a pyrimidine base.

An "oligonucleotide" refers to a nucleic acid polymer that includes at least two, but typically 5-50 nucleotides and more typically, between 15 and 35 nucleotides. The exact size of an oligonucleotide generally depends on various factors, including the ultimate function or use of the oligonucleotide. Oligonucleotides may be prepared by any suitable method known in the art, including, for example, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103:3185-3191; automated synthesis methods; the solid support method of U.S. Pat. No. 4,458, 066 or any other chemical method known in the art.

A "primer nucleic acid" or "primer" is an oligonucleotide that can hybridize to a template nucleic acid and permit chain extension or elongation using a nucleotide incorporating biocatalyst, such as a polymerase. Although other primer lengths are sometimes utilized, primers typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. However, the success of the extension generally requires greater complementarity (i.e. fewer mismatches with the template) at the 3'-end of the primer. A primer nucleic acid can be labeled, if desired, by incorporating a label detectable by radiological, spectroscopic, photochemical, biochemical, immunochemical, or chemical techniques.

An "extended primer" refers to a primer to which one or more additional nucleotides have been added. "Primer extension" is the action of the enzyme by which additional nucleotides are added to the primer.

A "template nucleic acid", "template" or "target" refers to a nucleic acid to which a primer nucleic acid can hybridize and be extended under suitable conditions. In the context of nucleic acid amplification, "target" is preferably a region of double stranded nucleic acid, consisting of the sequences at least partially complementary to at least two primer sequences and the intervening sequence. A target can also be a single stranded nucleic acid, consisting of a sequence at least partially complementary to one primer and a sequence partially identical to the second primer. Template nucleic acids can exist as isolated nucleic acid fragments or be a part of a larger nucleic acid fragment. Target nucleic acids can be derived or isolated from essentially any source, such as cultured microorganisms, uncultured microorganisms, complex biological mixtures, tissues, sera, ancient or preserved tissues or samples, environmental isolates or the like. Further, template nucleic acids optionally include or are derived from cDNA, RNA, genomic DNA, cloned genomic DNA, genomic DNA libraries, enzymatically fragmented DNA or RNA, chemically fragmented DNA or RNA, physically fragmented DNA or RNA, or the like. Template nucleic acids can also be chemically synthesized using techniques known in the art.

As used herein, a "gene" refers to any segment of DNA associated with a biological function. Thus, genes include coding sequences and optionally, the regulatory sequences required for the expression of the coding sequences.

Nucleic acids are "extended" or "elongated" when additional nucleotides are incorporated into the nucleic acids, for example by a nucleotide incorporating biocatalyst, at the 3' end of a nucleic acid.

A "moiety" or "group" refers to one of the portions into which something, such as a molecule, is divided (e.g., a functional group, substituent group, or the like). For example, a nucleotide typically comprises a base group (e.g., adenine, thymine, cytosine, guanine, uracil, or an analog), a sugar moiety, and one or more phosphate groups.

An "alkyl group" refers to a linear, branched, or cyclic saturated hydrocarbon moiety and includes all positional isomers, e.g., methyl, ethyl, propyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "alkoxy group" refers to an alkyl group that comprises an oxygen atom and includes, e.g., methoxy, ethoxy, propoxy, butoxy, pentoxy, heptyloxy, octyloxy, and the like.

An "aryl group" refers to a substituent group of atoms or moiety that is derived from an aromatic compound. Exemplary aryl groups include, e.g., phenyl groups, or the like. Aryl groups optionally include multiple aromatic rings (e.g., diphenyl groups, etc.). In addition, an aryl group can be substituted or unsubstituted.

An "aryloxy group" refers an aryl group that comprises an oxygen atom and includes, e.g., phenoxy, chlorophenoxy, methylphenoxy, methoxyphenoxy, butylphenoxy, pentylphenoxy, benzyloxy, and the like.

An "alkyl-aryl group" refers to a group that comprises alkyl and aryl moieties. Examples of the alkyl-aryl groups include benzyl groups, tolyl groups and xylyl groups.

An amplification assay is "selective" or "allele-selective" if it yields a predominance (i.e., a majority but less than 100%) of one product over other possible products. An assay is described as "allele-selective" as long as amplification of the undesired (mismatched) variant of the target sequence is detectable. The term "specific" or "allele-specific" amplification assay is used if one of the possible products is formed exclusively. The assay where amplification of the undesired (mismatched) target is undetectable is called "allele-specific." As the methods of detection become more sensitive, some assays previously known to be allele-specific, turn out to be allele-selective, i.e. some amplification of undesired variants of the target becomes detectable. Therefore, the term "allele-specific" is meant to encompass both strictly allele-specific, as well as allele-selective amplification.

A "genotype" refers to all or part of the genetic constitution of a cell or subject, or group of cells or subjects. For example, a genotype includes the particular mutations and/or alleles (e.g., polymorphisms, such as single nucleotide polymorphisms (SNPs) or the like) present at a given locus or distributed in a genome.

A "nucleotide incorporating biocatalyst" or "nucleotide incorporating enzyme" refers to a catalyst (or enzyme) that catalyzes the incorporation of nucleotides into a nucleic acid. Exemplary nucleotide incorporating enzymes include, DNA polymerases, RNA polymerases, terminal transferases, reverse transcriptases, telomerases and the like.

A "thermostable enzyme" refers to an enzyme that is stable (i.e., resists breakdown or denaturation) and retains sufficient catalytic activity when subjected to elevated temperatures for selected periods of time. For example, a thermostable polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" enzyme refers to an enzyme comprising an amino acid polymer in which at least one monomer differs from the reference sequence, such as a native or wild-type form of the enzyme or another modified form of the enzyme. Exemplary modifications include monomer insertions, deletions, and substitutions. Modified enzymes also include chimeric enzymes that have identifiable component sequences (e.g., structural or functional domains, etc.) derived from two or more parents. Also included within the definition of modified enzymes are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

A polymerase that "substantially lacks 5'-3' nuclease activity" refers to a polymerase that has 50% or less (e.g., <25%, <20%, <15%, <10%) 5'-3' nuclease activity than Taq DNA polymerase. Methods of measuring 5'-3' nuclease activity and conditions for measurement are well known in the art. See, e.g., U.S. Pat. No. 5,466,591. Examples of DNA polymerases substantially lacking 5' to 3' nuclease activity include the Klenow fragment of *E. coli* DNA polymerase I; a *Thermus aquaticus* DNA polymerase (Taq) lacking the N-terminal 235 amino acids (e.g., as described in U.S. Pat. No. 5,616,494 and commonly referred to in the art as the "Stoffel fragment"). Other examples include a thermostable DNA polymerase having sufficient deletions (e.g., N-terminal deletions), mutations, or modifications so as to eliminate or inactivate the domain responsible for the 5'-3' nuclease activity. See, e.g., U.S. Pat. No. 5,795,762.

A "label" refers to a moiety attached (covalently or non-covalently), to a molecule and capable of providing information about the molecule. Exemplary labels include fluorescent labels, colorimetric labels, chemiluminescent labels, bioluminescent labels, radioactive labels, massmodifying groups, antibodies, antigens, biotin, haptens, and enzymes (including peroxidase, phosphatase, etc.).

A "hot start", in the context of a nucleic acid amplification reaction, refers to a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol.

A "Watson-Crick base pairing" or simply "base pairing" refers to "conventional" hydrogen bonding within a double-stranded nucleic acid molecule. Watson-Crick base pairing is hydrogen bonding between adenine and thymine, between guanine and cytosine, between adenine and uracil, and between analogs of these bases.

The terms "scorpion" or "scorpion-like" denote unimolecular primer-probe combination as described in Whitcombe et al., (1999). Detection of PCR products using self-probing amplicons and fluorescence, Nature Biotech. 17:804-807. Scorpion or scorpion-like primers within the meaning of the present disclosure incorporate the typical elements of the scorpion, namely a probe portion, a stem loop portion and a primer portion. An example of "scorpion" or "scorpion-like" unimolecular primer-probe format.

As mentioned above, in one embodiment, the present disclosure provides a method of allele-specific amplification of a target sequence, which exists in the form of several variant sequences in a sample, including providing a blocking oligonucleotide comprising a 5' terminus, a 3' terminus, and at least one nucleotide with a base covalently modified at the exocyclic amino group, the blocking oligonucleotide being perfectly complementary to a wild type (WT) sequence when hybridized forming a first complex having a first melting temperature (Tm), the blocking oligonucleotide being partially non-complementary, at one or more nucleotides, to a target mutant (MT) sequence when hybridized forming a second complex having a second melting temperature (Tm), wherein the first Tm is higher than the second Tm, the blocking oligonucleotide being blocked at the 3' terminus prohibiting extension; and performing an amplifying step at a temperature higher than the second Tm but lower than the first Tm utilizing a polymerase lacking 5'-3' nuclease activity, the amplifying step comprising contacting the sample with a set of primers to produce an amplification product if the WT sequence and/or the target MT sequence is present in the sample, wherein the blocking oligonucleotide becomes unhybridized from the target MT sequence during the amplification step but remains hybridized with the WT sequence inhibiting amplification of the WT sequence.

The blocking oligonucleotide can include, e.g., 10-50, or, e.g., 15-35 nucleotides, being perfectly complementary to a WT sequence, and being partially non-complementary, at one or more nucleotides, to a target MT sequence. The partial non-complementary region of the blocking oligonucleotide with respect to the target MT sequence, may include, 1, 2, or more nucleotides located anywhere along the length of the blocking oligonucleotide, e.g., at the 5'-terminal nucleotide, or an internal position(s) between the two termini. The blocking oligonucleotide of the present disclosure may include one or more nucleotides with a base, covalently modified at the exocyclic amino group. In some embodiments, the modified-base nucleotide occurs between 1 and 5, e.g., 3 nucleotides upstream of the the site of non-complementary nucleotide of the blocking oligonucleotide (also designated as −1, −2, −3, −4, −5 or N−1, N−2, N−3, N−4, N−5 positions herein). In other embodiments, the modified-base nucleotide is the site of non-complementary nucleotide of the blocking oligonucleotide. In some embodiments, the modified-base nucleotide occurs both at the site of non-complementary nucleotide of the blocking oligonucleotide and at least once more, elsewhere within the oligonucleotide.

The nucleotides with covalent modifications of the exocyclic amino groups have been described in U.S. Pat. No. 6,001,611, which is incorporated herein by reference. The synthesis of such nucleotides, and oligonucleotides incorporating such nucleotides are also described in the '611 patent.

According to the present disclosure, a suitable modification of the exocyclic amino group may be selected based on the presence of the following properties: (1) the modification interferes with but does not prevent Watson-Crick base pairing of the modified base with the complementary base in the double-stranded nucleic acid; and (2) the modification decreases the melting temperature of blocking oligonucleotide containing the modified base at or near the site of non-complementary nucleotide of the blocking oligonucleotide relative to the target MT seqeune as compared to the perfect complementary to the WT sequence. For example, the inclusion of a tert butyl benzyl group on the exocyclic amins of a deoxyadenosine close to the middle of an oligonucleotide 30 bases long would lower the Tm of a hybrid against a perfectly matched template by between 2 and 4 degrees Celsius. However, the Tm of a hybrid of such an oligonucleotide would be reduced by 6 or more degrees when hybridized to a sequence with a mismatch complementary to the site of the modification. The inclusion of multiple modifiers would have only a marginal incremental change in Tm against the Wild Type sequence, but would further destabilize the hybrid with mismatches present. The inclusion of the modified base has an insignificant impact on the Tm of the probe to its perfect match with WT sequence; about 2° C. lower Tm. However, this modification provides an additional destabilization of the probe to the MT sequence, where the synergistic effects of the destabilization of the mismatch and, e.g., a benzyl group lowers the Tm of the probe to the MT sequence by about 5° C. to 10° C. The additional destabilization imparts much greater discrimination in the ability of the probe to suppress the amplification of the WT sequence while still allowing efficient amplification of the desired MT sequence. The term "about" in the context of a stated difference in Tm may include exactly the stated temperature difference in Tm, and also include a temperature difference having in Tm of 1° C., 2° C., or a fraction thereof, plus or minus the stated temperature difference.

The blocking oligonucleotide of the present disclosure can be blocked at the 3' terminus in order to prohibit extension, in otherwords inhibit incorporation of the blocking oligonucleotide into a primer extension product. The blocking can be achieved in different ways, e.g., by adding a chemical moiety, e.g., a phosphate group to the 3' hydroxyl of the last nucleotide, or by removing the 3'-hydroxyl group, or by the inclusion of non-nucleoside analogs of the last nucleotide.

The examples of exocyclic amino groups include the amino groups in the 6-position of adenosine, 2-position of guanosine and 4-position of cytosine. Exocyclic amino groups that take part in base pairing with the complementary nucleic acid strand may also occur in various unconventional nitrogenous bases in nucleotides. Examples of nucleosides with unconventional bases include, without limitation, 3-methyladenosine, 7-methylguanosine, 3-methylguanosine, 5-methylcytidine, and 5-hydroxymethylcytidine. Suitable modifications of exocyclic amino groups of such unconventional bases may also be selected according to the empirical method of the present disclosure.

The structures of the modified nucleotides containing a modified adenine, guanine, and cytosine base, respectively, are shown below,

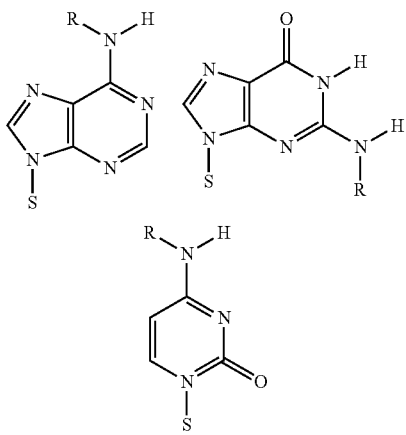

where S represents the sugar moiety, and R represents the modifier group. A variety of modifier groups are envisioned which possess the four properties outlined above. In certain embodiments, modifier groups have the structure:

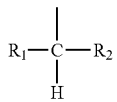

wherein $R_1$ and $R_2$ are independently selected from the group consisting of hydrogen, alkyl, alkoxy, unsubstituted or substituted aryl and phenoxy.

Alkyl groups may be branched or unbranched

Alkyl groups can be $C_1$-$C_{20}$ alkyls, for example $C_1$-$C_{10}$ alkyls.

Alkoxy groups can be $C_1$-$C_{20}$ alkoxy, for example $C_1$-$C_{10}$ alkoxy.

Aryl can be unsubstituted or substituted phenyl or naphthyl.

In one embodiment, R is a benzyl group or a substituted benzyl group. In certain embodiments, substituted benzyl groups can have the following structure:

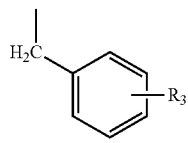

wherein $R_3$ represents a $C_1$-$C_6$ branched or unbranched alkyl group, more preferably a $C_1$-$C_4$ branched or unbranched alkyl group, an alkoxy group, or a nitro group. Preferably, $R_3$ is attached in the para-position.

In some embodiments, the modifier groups are represented by structures shown below:

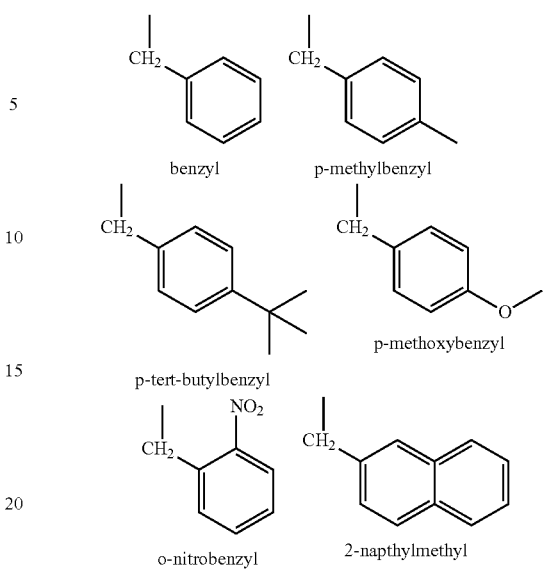

In general, empirical selection of a particular suitable modifier group from the class of compounds described herein can be carried out routinely by one of skill in the art, based on the presence of the four properties listed above. Preferably, suitability of a particular group is determined empirically by using the blocking oligonucleotide with modified nucleotides in an allele-specific amplification reaction. The suitability of the modification is indicated by the increased selectivity of the reaction utilizing a blocking oligonucleotide with the base modification, when compared to an identical reaction with an unmodified blocking oligonucleotide.

In some embodiments, the amplification involves the polymerase chain reaction, i.e., repeated cycles of template denaturation, annealing (hybridization) of the oligonucleotide primer to the template, and extension of the primer by the nucleotide-incorporating biocatalyst. In some embodiments, the annealing and extension occur at the same temperature step.

In some embodiments, the amplification reaction involves a hot start protocol. Many hot start protocols are known in the art, for example, the use of wax, separating the critical reagents from the rest of the reaction mixture (U.S. Pat. No. 5,411,876), the use of a nucleic acid polymerase, reversibly inactivated by an antibody (U.S. Pat. No. 5,338,671), a nucleic acid polymerase reversibly inactivated by an oligonucleotide that is designed to specifically bind its active site (U.S. Pat. No. 5,840,867) or the use of a nucleic acid polymerase with reversible chemical modifications, as described e.g. in U.S. Pat. Nos. 5,677,152 and 5,773,528.

In some embodiments, the allele-specific amplification assay is the real-time PCR assay. In a real-time PCR assay, the measure of amplification is the "cycles to threshold" or Ct value. An earlier Ct value reflects the rapid achievement of the threshold level and thus a more efficient amplification. The later Ct value may reflect inefficient or inhibited amplification. In the context of an allele-specific real-time PCR assay, the difference in Ct values between the matched and the mismatched templates is a measure of the discrimination between the alleles or the selectivity of the assay.

The allele-specific amplification assay may use enzymes, substantially or entirely lacking the 5'-3' nuclease activity, such as described in U.S. Pat. No. 5,795,762. One example of such an enzyme is ΔZ05 polymerase. The allele-specific amplification assay may also use employ an enzyme without the proof-reading (3'-5'-exonuclease) activity, such as for example, Stoffel fragment of Taq DNA polymerase. It may sometimes be desirable to have an enzyme with a "hot start" capability, such as the reversibly modified enzymes described in U.S. Pat. Nos. 5,677,152 and 5,773,528. One example of a hot-start enzyme is ΔZ05-Gold polymerase.

Detection of the amplification products may be accomplished by any method known in the art. These methods include the use of labeled primers and probes as well as various nucleic acid-binding dyes. The means of detection may be specific to one variant of the target sequence, or may be generic to all variants of the target sequence or even to all double stranded DNA. The non-specific detection methods may be used where the amplification of the undesired variants of the target is minimal and expected to fall below the detection limit of the method.

The amplification products may be detected after the amplification has been completed, for example, by gel electrophoresis of the unlabeled products and staining of the gel with a nucleic acid-binding dye. Alternatively, the amplification products may carry a radioactive or a chemical label, either by virtue of incorporation during synthesis or by virtue of being the extension products of a labeled primer. After, or during electrophoresis, the labeled amplification products may be detected with suitable radiological or chemical tools known in the art. After electrophoresis, the product may also be detected with a target-specific probe labeled by any one of the methods known in the art. The labeled probe may also be applied to the target without electrophoresis, i.e. in a "dot blot" assay or the like.

In other embodiments, the presence of the amplification product may be detected in a homogeneous assay, i.e. an assay where the nascent product is detected during the cycles of amplification, or at least in the same unopened tube, and no post-amplification handling is required. A homogeneous amplification assay has been described for example, in U.S. Pat. No. 5,210,015. Homogeneous amplification assay using nucleic acid-intercalating dyes has been described for example, in U.S. Pat. Nos. 5,871,908 and 6,569,627. The homogeneous assay may also employ fluorescent probes labeled with two interacting fluorophores, such as "molecular beacon" probes (Tyagi et al., (1996) Nat. Biotechnol., 14:303-308) or fluorescently labeled nuclease probes (Livak et al., (1995) PCR Meth. Appl., 4:357-362). In certain variations of these technologies, an amplification product may also be identified by virtue of its distinctive melting temperature, see U.S. Pat. Nos. 5,871,908 and 6,569,627. The amplification products may also be detected using a unimolecular primer-probe combination termed "scorpion." Whitcombe et al., (1999) Detection of PCR products using self-probing amplicons and fluorescence, *Nature Biotech.* 17:804-807.

In another embodiment, kits are provided for conducting allele-specific amplification according to the present disclosure. The kit generally includes assay-specific components as well as components generally required for performing DNA amplification assays. As the assay-specific components, the allele-specific amplification kit of the present disclosure typically includes at least one allele-specific oligonucleotide including a sequence having a 5' terminus and a 3' terminus being blocked to prohibit extension, the sequence being perfectly complementary to a WT sequence when hybridized forming a first complex having a first Tm, and being partially non-complementary, at one or more nucleotides, to a target MT sequence when hybridized forming a second complex having a second Tm, wherein the first Tm is higher than the second Tm, and also having one or more nucleotides with a base covalently modified at the exocyclic amino group, optionally, a control nucleic acid sequence comprising an amount of at least one variant of the control target sequence, at least partially complementary to the oligonucleotides enclosed in the kit. In some embodiments, more than one variant of the control nucleic acid sequence may be enclosed. As the components generally required for nucleic acid amplification, the kit of the present disclosure typically includes one or more of a nucleotide incorporating biocatalyst, nucleic acid precursors, such as nucleoside triphosphates (deoxyribonucleoside triphosphates or ribonucleoside triphosphates), optionally, a pyrophosphatase, for minimizing pyrophosphorolysis of nucleic acids, a uracil N-glycosylase (UNG) for protection against carry-over contamination of amplification reactions, premade reagents and buffers necessary for the amplification reaction and detection, and a set of instructions for conducting allele-specific amplification of the present disclosure.

Figure 1B:
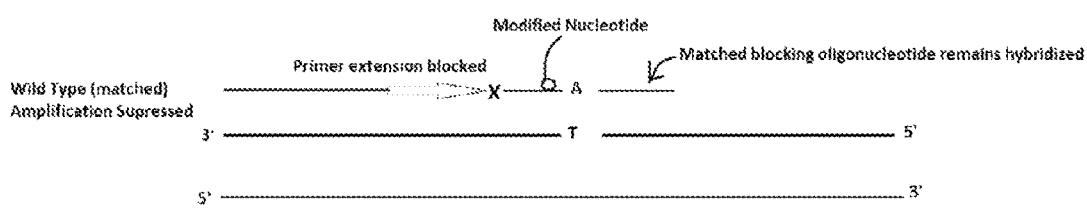

Without being bound by a particular theory, the inventor hypothesizes that the covalent base modifications of the present disclosure, especially the bulky groups, destabilize, but do not entirely disrupt hydrogen bonding in the context of Watson-Crick base pairing between the primer and the template nucleic acid. When the modification is combined with a non-complementary base at the same or nearby position within the blocking oligonucleotide (as on the mutant or "mismatched" variant of the target sequence), the combined weakness of hydrogen bonding destabilizes the blocking oligonucleotide-target nucleic acid complex to the extent that the extension of the primer by the polymerase lacking 5'-3' nuclease activity is not blocked because the blocking oligonucleotide melts off of the target MT sequence. However, when the modification of the base is present alone, without the non-complementary base (as on the wild type or "matched" variant of the target sequence), there is less weakness of hydrogen bonding and less destabilization the blocking oligonucleotide-target nucleic acid complex to the extent that the extension of the primer by the polymerase lacking 5'-3' nuclease activity is blocked because the blocking oligonucleotide does not melt off of the target sequence and remains hybridized and blocking extension of the primer. FIG. 1 is a diagram illustrating the position of the polymorphism and the blocking oligonucleotide modifications, and their role in allowing the amplification or the unmatched target mutant sequence, but inhibiting the amplification of the matched wild type sequence.

The following examples and figures are provided to aid the understanding of the present invention, the true scope of which is set forth in the appended claims. It is understood that modifications can be made in the procedures set forth without departing from the spirit of the invention.

EXAMPLES

In this Example, a method is described for allele-specific amplification of a target sequence, which exists in the form of several variant sequences in a sample. The method involves providing a blocking oligonucleotide including a 5' terminus, a 3' terminus, and at least one nucleotide with a base covalently modified at the exocyclic amino group. The blocking oligonucleotide can be designed to be perfectly complementary to a wild type (WT) sequence when hybridized forming a first complex having a first melting temperature (Tm), the blocking oligonucleotide being partially non-complementary, at one or more nucleotides, to a target mutant (MT) sequence when hybridized forming a second complex having a second melting temperature (Tm). The first Tm is higher than the second Tm, and the blocking oligonucleotide is blocked at the 3' terminus prohibiting extension.

The method also involves performing an amplifying step at a temperature higher than the second Tm but lower than the first Tm utilizing a polymerase lacking 5'-3' nuclease activity. The amplifying step includes contacting the sample with a set of primers to produce an amplification product if the WT sequence and/or the target MT sequence are present in the sample. In this way, the blocking oligonucleotide becomes unhybridized from the target MT sequence during the amplification step but remains hybridized with the WT sequence inhibiting amplification of the WT sequence.

The nucleotide having a covalently modified base at the exocyclic amino group can be located at positions −5, −4, −3, −2, −1, or 0 relative to the site of non-complementary nucleotide of the blocking oligonucleotide. The modified nucleotide can be a modified guanine (G*), which it is still capable of hybridizing with the complementary C base in the WT sequence. The inclusion of this modifier has an insignificant impact on the Tm of the probe to its perfect match with WT sequence; about 2° C. lower Tm. However, this modification provides an additional destabilization of the probe to the MT sequence, where the synergistic effects of the destabilization of the mismatch and the benzyl group lowers the Tm of the probe to the MT sequence by about 5° C. to 10° C. The additional destabilization imparts much greater discrimination in the ability of the probe to suppress the amplification of the WT sequence while still allowing efficient amplification of the desired MT sequence.

The following provides a comparison for the change in Tm for respective modified nucleotides located at positions −5, −4, −3, −2, −1, or 0 relative to the site of non-complementary nucleotide of the blocking oligonucleotide. When the modified nucleotide is located at position 0, the difference in Tm is about 4° C. lower; when the modified nucleotide is located at position −1, the difference in Tm is about 8° C. lower; when the modified nucleotide is located at position −2, the difference in Tm is about 6° C. lower; when the modified nucleotide is located at position −3° C. lower, the difference in Tm is about 5° C. lower; when the modified nucleotide is located at position −4, the difference in Tm is about 4° C. lower; when the modified nucleotide is located at position −5, the difference in Tm is about 3° C. lower.

While the invention has been described in detail with reference to specific examples, it will be apparent to one skilled in the art that various modifications can be made within the scope of this invention. Thus the scope of the invention should not be limited by any of the examples described herein, but by the claims presented below. All publications including patent applications and patents cited in this application are incorporated by reference in their entirety for all purposes to the same extent as if each individual publications were individually indicated to be incorporated by reference for all purposes.

The invention claimed is:

1. A method of allele-specific amplification of a target sequence, which exists in the form of several variant sequences in a sample, comprising:
   providing a blocking oligonucleotide comprising a 5' terminus, a 3' terminus, and at least one nucleotide with a base covalently modified at the exocyclic amino group, the blocking oligonucleotide being perfectly complementary to a wild type (WT) sequence when hybridized forming a first complex having a first melting temperature (Tm), the blocking oligonucleotide being partially non-complementary, at one or more nucleotides, to a target mutant (MT) sequence when hybridized forming a second complex having a second melting temperature (Tm), wherein the first Tm is higher than the second Tm, the blocking oligonucleotide being blocked at the 3' terminus prohibiting extension; and performing an amplifying step at a temperature higher than the second Tm but lower than the first Tm utilizing a polymerase lacking 5'-3' nuclease activity, the amplifying step comprising contacting the sample with a set of primers to produce an amplification product if the WT sequence and/or the target MT sequence is present in the sample, wherein the blocking oligonucleotide becomes unhybridized from the target MT sequence during the amplification step but remains hybridized with the WT sequence inhibiting amplification of the WT sequence.

2. The method of claim 1, wherein the nucleotide having a covalently modified base at the exocyclic amino group is located at positions −5, −4, −3, −2, −1, or 0 relative to the site of non-complementary nucleotide of the blocking oligonucleotide.

3. The method of claim 1, wherein the base covalently modified at the exocydic amino group is selected from a group consisting of $N^6$-benzyl-adenine, $N^6$-para-tert-butyl-benzyl adenine, $N^2$-alkyl-guanine and $N^4$-benzyl-cytosine.

4. The method of claim 1, further comprising a step of detecting the amplification product.

5. The method of claim 1, wherein the polymerase is selected from a group consisting of Stoffel fragment of Taq DNA polymerase, ΔZ05 DNA polymerase, and ΔZ05-Gold DNA polymerase.

6. The method of claim 1, wherein the structure of the nucleotide with a base covalently modified at the exocydic amino group is selected from the group consisting of:

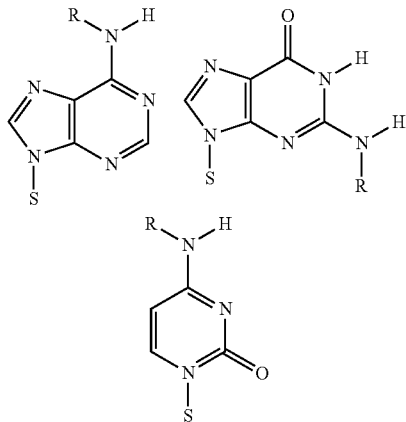

wherein S represents a sugar moiety, and R represents a modifier group.

7. The method of claim 1, wherein the base covalently modified at the exocydic amino group comprises a modifier of the following formula:

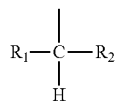

wherein $R_1$ and $R_2$ are independently selected from the group consisting of hydrogen, alkyl, alkoxy, unsubstituted or substituted aryl and phenoxy.

8. The method of claim 2, wherein the modifier has the following formula:

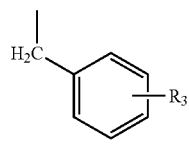

wherein $R_3$ is selected from the group consisting of $C_1$-$C_6$ alkyl, alkoxy and nitro.

9. The method of claim 8, wherein the modifier is selected from the group consisting of:

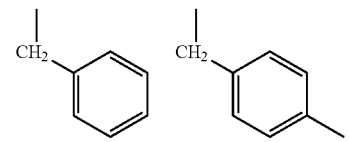

benzyl            p-methylbenzyl

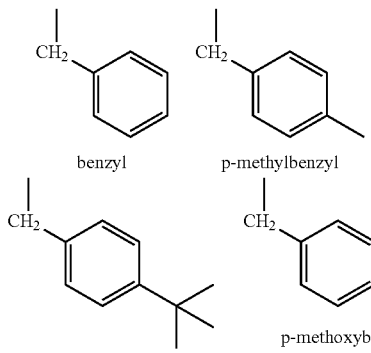

p-tert-butylbenzyl     p-methoxybenzyl

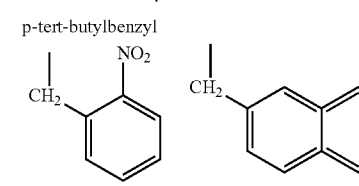

o-nitrobenzyl          2-napthylmethyl

* * * * *